United States Patent [19]
Campbell et al.

[11] Patent Number: 4,777,275
[45] Date of Patent: Oct. 11, 1988

[54] PROCESS OF PREPARING HIGHER ORDER CUPRATE COMPLEXES

[75] Inventors: Arthur L. Campbell, Glenview; James R. Behling, Lindenhurst, both of Ill.

[73] Assignee: G. D. Searle & Co., Chicago, Ill.

[21] Appl. No.: 59,695

[22] Filed: Jun. 9, 1987

[51] Int. Cl.$^4$ .............................................. C07F 1/08
[52] U.S. Cl. .................................. 556/112; 549/206; 549/3
[58] Field of Search ...................... 556/112; 549/206, 3

[56] References Cited

U.S. PATENT DOCUMENTS

| Re. 30,287 | 5/1980 | Marx et al. | 556/112 X |
|---|---|---|---|
| 3,965,143 | 6/1976 | Collins et al. | 556/112 X |
| 4,271,314 | 6/1981 | Collins | 560/121 |
| 4,322,543 | 3/1982 | Collins | 556/436 |
| 4,499,296 | 2/1985 | Collins | 560/118 |
| 4,529,812 | 7/1985 | Collins | 560/121 |
| 4,578,505 | 3/1986 | Collins | 560/118 |

OTHER PUBLICATIONS

Lipshutz "Applications of Higher Order Mixes Organocuprates to Organic Synthesis:, Synthesis, 4," p. 325 (1987).
Bindra and Bindra, "Prostaglandin Synthesis", Academic Press, Inc., N.Y. Chapter 7, pp. 99–108.
Collins, J. Med. Chem., 29, 437 (1986).
Corey et al., J.A.C.S., 94, 7210–11 (1972).

Primary Examiner—Paul F. Shaver
Attorney, Agent, or Firm—Mary Jo Kanady; Paul D. Matukaitis

[57] ABSTRACT

This invention encompasses a process for preparing higher order cuprate complexes which contain a carbanion for the formation of carbon to carbon bonds in reactions such as 1,4-conjugate addition. The complex is formed by reacting a first cuprate complex with a stannane such that the carbanion to be used to form carbon to carbon bonds is transferred from the stannane to the first cuprate complex to form a different higher order cuprate complex. This process permits the in situ preparation of a higher order cuprate complex having the carbanion desired to be used in a synthetic reaction. Higher order cuprate complexes prepared by this process are particularly useful for the efficient preparation of pharmacologically active prostaglandins.

8 Claims, No Drawings

PROCESS OF PREPARING HIGHER ORDER CUPRATE COMPLEXES

BACKGROUND OF THE INVENTION

I. Field of the Invention

This invention is in the field of preparing higher order cuprate complexes from alkyl, vinyl, benzyl, phenyl or allyl stannane compounds which complexes are useful as reactive intermediates in organic synthesis. In particular the process and compounds of this invention are useful for the addition of the omega chain to cyclopentenones in the synthesis of prostaglandins.

II. Prior Art

The state of the art of higher order cuprate complexes is summarized in *Synthesis*, #4, p. 325, (1987) where higher order cuprate complexes of the formulae $R_tRCu(CN)Li_2$, $R_tCu(2\text{-thienyl})CNLi_2$, and $R_tRCu(SCN)Li_2$ and their use are disclosed. $R_t$ represents the group transferred to an organic compound to form a carbon to carbon bond in a subsequent reaction with the complex.

U.S. Pat. No. 4,499,296 describes the preparation of a large number of prostaglandins prepared by the sequence of reactions set out in the following steps:

(i) a stannane compound of the formula

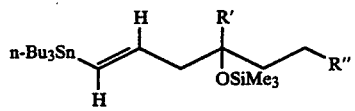

is reacted with alkyl lithium in one reaction vessel;

(ii) an organo copper compound is formed in a separate vessel;

(iii) the reagents formed in (i) and (ii) are mixed together and added to a cyclopentenone:

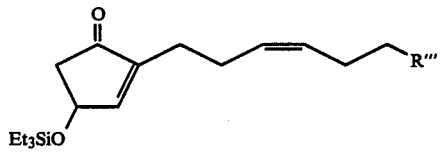

to provide prostaglandins of formula I

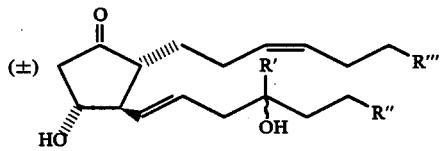

wherein,

R''' is $-CO_2R''''$;

R'''' is hydrogen or lower alkyl containing 1 to 6 carbon atoms;

R' is lower alkyl containing 1 to 6 carbon atoms, vinyl or ethynyl;

R'' is alkyl or cycloalkyl containing 3 to 5 carbon atoms; and the wave line represents R,S stereochemistry.

JACS 94 7210 (1972) describes lithium copper vinyl complexes. *Prostaglandin Synthesis*, Academic Press, 1977, Chapt. 7 describes prostaglandin synthesis generally. U.S. Pat. Nos. 4,449,296; 4,322,543; 4,578,505; and 4,271,314 describe organotin intermediates in the preparation of prostaglandins.

BRIEF DESCRIPTION OF THE INVENTION

This invention encompasses a process for preparing a higher order cuprate complex comprising bringing into reactive contact a first cuprate complex of the formula:

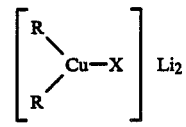

or $[R-Cu-(CN)_2]LiN(R^1)_4$ wherein:

(a) X is $-CN$, $-SCN$, $-O-SO_2CF_3$ or $-S-$phenyl;

(b) each R is independently lower alkyl, alkenyl, phenyl, naphthyl, phenanthryl, or thienyl, provided that (i) each of the aforementioned radicals may be substituted with non-interfering substituents and (ii) only one R in the first cuprate complex may be alkenyl, phenyl, naphthyl, phenanthryl, or thienyl; and (c) each $R^1$ is independently lower alkyl;

with a stannane compound of the formula:

$R_tSn(R^2)_3$ wherein $R_t$ is a carbanion for carbon to carbon bond formation reactions and is not the same as any R in the first cuprate complex and each $R^2$ is independently lower alkyl or $R_t$;

whereby $R_t$ replaces at least one R on Cu.

In accordance with the present invention it is not necessary to first react an organo stannane compound with alkyl lithium in one reaction vessel, prepare an alkyl copper in a second reaction vessel and then combine the two reagents to form the cuprate complex suitable for reactions such as 1,4-conjugate addition to cyclopentenones. In the present invention, a higher order cuprate complex is prepared in situ by transferring directly from a stannane compound to a cuprate complex the ligand ($R_t$) which is desired in a subsequent synthetic organic reaction to form a new carbon to carbon bond. This in situ preparation is exemplified in the following reaction (Scheme 1);

Scheme 1

$CuX + 2RLi$

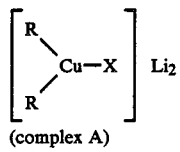

(complex A)

 $R_tSn(R^2)_3$

-continued
Scheme 1

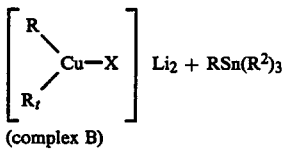

(complex B)

It is noted that the order of addition of RLi or $R_tSn(R^2)_3$ is in general not critical and can be reversed.

Complex B of Scheme 1 is useful in a wide variety of organic synthetic reactions to add $R_t$ to receptive compounds. Examples of these reactions are illustrated as follows:

(i) 1,4 conjugate addition to $\alpha,\beta$ unsaturated ketones

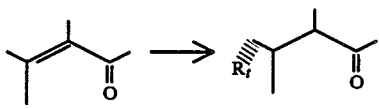

(ii) epoxide opening

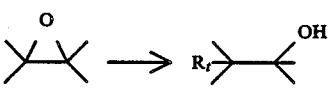

(iii) halide, tosylate, and mesylate displacement

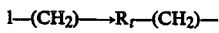

DETAILED DESCRIPTION OF THE INVENTION

This invention encompasses a higher order reactive cuprate complex prepared by the process of bringing into reactive contact a first cuprate complex of the formula

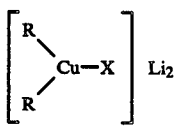

or

wherein:

(a) X is —CN, —SCN, —O—SO$_2$CF$_3$ or —S—phenyl
(b) each R is independently lower alkyl, alkenyl, phenyl, naphthyl, phenanthryl, or thienyl, provided that (i) each of aforementioned radicals may be substituted with non-interfering substituents and (ii) only one R in the first cuprate complex may be alkenyl, phenyl, naphthyl, phenanthryl, or thienyl; and
(c) each $R^1$ is independently lower alkyl;
with a stannane compound of the formula:

$R_tSn(R^2)_3$ wherein $R_t$ is a carbanion for carbon to carbon bond formation reactions and is not the same as any R in the first cuprate complex and each $R^2$ is independently lower alkyl or $R_t$;
whereby $R_t$ replaces at least one R on Cu.

By lower alkyl is meant straight or branched chain alkyl having 1 to 6 carbon atoms and cycloalkyl having 3 to 6 carbon atom.

By non-interfering substituent is meant substituents such as lower alkyl, lower alkoxy, halo, lower alkanoyl, phenyl, cyano, phenoxy and the like which do not react with the cuprate complex or sterically and/or electronically hinder the reaction.

By carbanion is meant a carbanion useful in carbon to carbon bond formation in addition reactions such as 1,4-conjugate addition, addition to epoxides, and displacement reactions. More specifically, $R_t$ represents a broad range of carbanions that will transfer in situ from stannane to displace an alkyl on a cuprate complex in the process of the present invention. $R_t$ includes carbanions having 1 to 20 carbon atoms and which may have unsaturation. $R_t$ may have halo, lower alkoxy, phenoxy, cyano, lower alkanoyl, phenyl substituted with halo, lower alkoxy, lower alkyl, lower alkanoyl, cyano, phenyl and the like substituents. The $R_t$ carbanion may also be substituted with hydroxy or hydroxy protected with tri-lower-alkylsilyl, tetrahydropyranyl, or tetrahydrofuranyl.

Illustrative of classes of carbanions are those represented by $R_t$ equal to allyl, phenyl, benzyl, alkyl, and vinyl each of which may contain noninterfering substituents. Examples of stannane compounds containing such classes of carbanions are as follows:

$R_t$ = allyl:
BuSn(CH$_2$—CH=CH$_2$)$_3$
Bu$_2$Sn(CH$_2$—CH=CH$_2$)$_2$
Bu$_3$Sn(CH$_2$—CH=CH$_2$)
Sn(CH$_2$—CH=CH$_2$)$_4$ $R_t$ = Benzyl:
Bu$_3$Sn (p-methylbenzyl)
Bu$_3$Sn (p-methoxybenzyl)
Bu$_3$Sn (p-fluorobenzyl)
Bu$_3$Sn (m-fluorobenzyl)

$R_t$ = alkyl:
Me$_3$Sn (tertiary-butyl)
Me$_3$Sn (iodomethyl)
Bu$_3$Sn (methoxymethyl)
Bu$_3$Sn (cyanomethyl)
Bu$_3$Sn (acetylmethyl)
Bu$_3$Sn (phenylcarbonylmethyl)

$R_t$ = aryl:
Me$_3$SnPh
Bu$_3$SnPh

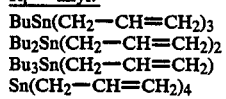

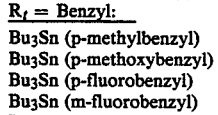

$R_t$ = vinyl:
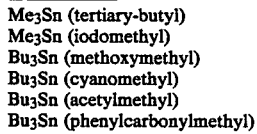

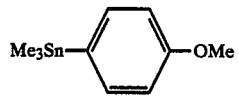

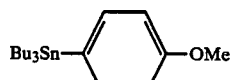

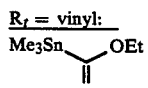

-continued

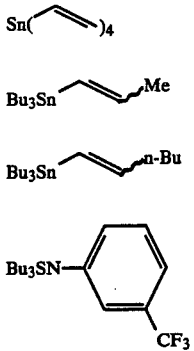

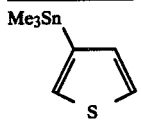

$R_t$ = thienyl:

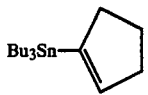

The higher order cuprate complex of this invention is generally formed in a suitable solvent, for example, in either an alkyl ether solvent where the alkyl groups have 1 to 6 carbon atoms, or in a cycloalkyl ether solvent having 4 to 6 carbon atoms such as tetrahydrofuran or tetrahydropyranes, or in alkane solvents having 5 to 18 carbons or mixtures thereof. Reaction temperature is generally not critical with the reactions of Scheme 1. These reactions are typically conducted at a temperature in the range of about −20° C. to about 30° C.

Referring to reaction Scheme 1, and by way of example, typically about two moles of alkyl lithium in a hydrocarbon or ether solvent is reacted with about one mole of copper cyanide or thiocyanide in tetrahydrofuran, for example, at about 0° C. to form Complex A, then about one mole of $R_tSn(R^2)_3$ in tetrahydrofuran is added to form higher order cuprate complex (Complex B). This Complex B can then be reacted with, for example, α,β-unsaturated cyclopentenone in tetrahydrofuran (about a one to one (1:1) molar ratio of tetrahydrofuran to cyclopentenone) at about −60° C. to 0° C. The 1,4-conjugate addition product is then isolated by art recognized techniques.

In a preferred embodiment, a cuprate complex of the formula

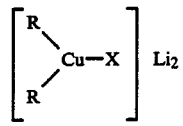

wherein one R is lower alkyl and one R is thienyl, and wherein X is —CN or —SCN, is reacted with a vinyl tin compound of the formula $$R^3-CH=CH-Sn(R^2)_3$$

wherein $R^3-CH=CH-$ is the omega chain of a natural or synthetic prostaglandin and wherein any hydroxy groups contained in said chain are optimally protected by tri-lower-alkylsilyl, tetrahydropyranyl or tetrahydrofuranyl. Each $R^2$ is independently lower alkyl. $R^3$ contains 1 to 10 carbon atoms which may have vinyl or alkynyl unsaturation. $R^3$ may contain cycloalkyl moieties where the cycloalkyl contains 3 to 6 carbon atoms. $R^3$ may be substituted with hydroxy, tri-lower-alkylsilyloxy, tetrahydropyranyloxy, tetrahydrofuranyloxy, fluoro, or phenoxy. These vinyl tin compounds are made by art recognized techniques. The procedure generally involves the following reaction:

$$R^3-\equiv-H + H-Sn(R^2)_3 \xrightarrow{h\nu} R^3-CH=CHSn(R^2)_3$$

U.S. Pat. Nos. 4,499,296; 4,322,543, 4,578,505; and 4,271,314 describe the procedures for making omega side chains for prostaglandins using such tin compounds. Illustrative of such tin compounds are:

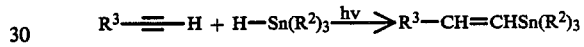

wherein $R^{2'}$ is hydrogen or lower alkyl and $R^2$ is lower alkyl and $R^5$ is lower alkyl containing 1 to 4 carbon atoms, cycloalkyl containing 3 to 6 carbon atoms, cycloalkylalkyl containing 4 to 7 carbon atoms, or cycloalkylalkenyl containing 5 to 7 carbon atoms.

Specific vinyl stannane compounds, which are useful for forming the higher order cuprate complexes of this invention and for making pharmacologically active prostaglandins, are the following compounds:

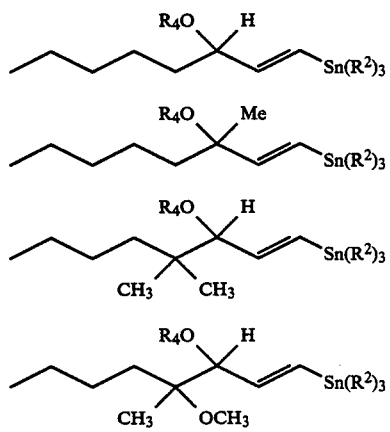

-continued

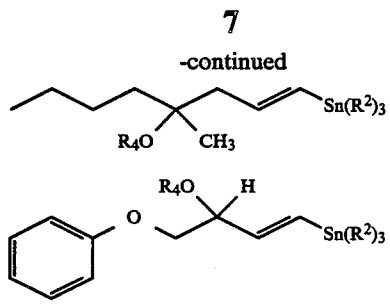

-continued

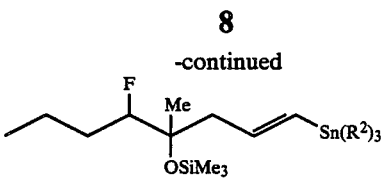

wherein $R^2$ is as defined in the immediately preceding paragraph and $R_4$ is tri-lower-alkylsilyl or tetrahydropyranyl or tetrhydrofuranyl.

Cuprate complexes derived from these vinyl tin compounds are useful for 1,4 addition to cyclopentenones as illustrated in Journal of Medicinal Chemistry, 29, 437 (1986) to form the following prostaglandins indicated in Table I:

TABLE 1

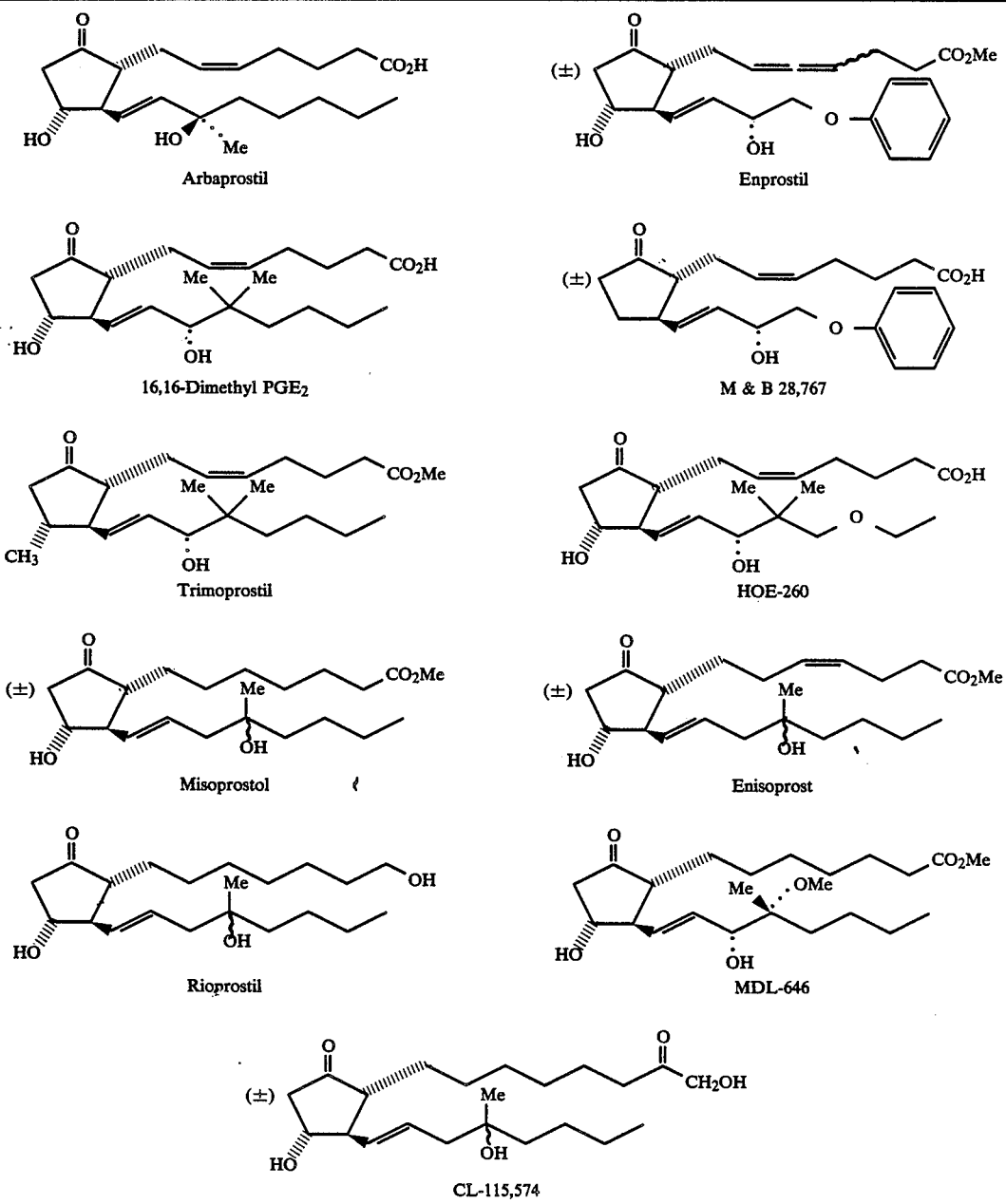

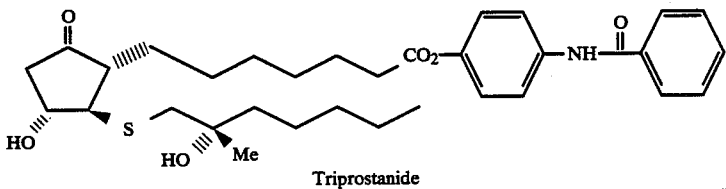
Triprostanide

DESCRIPTION OF THE PREFERRED EMBODIMENTS

The following scheme (Scheme 2) illustrates a preferred embodiment of the present invention:

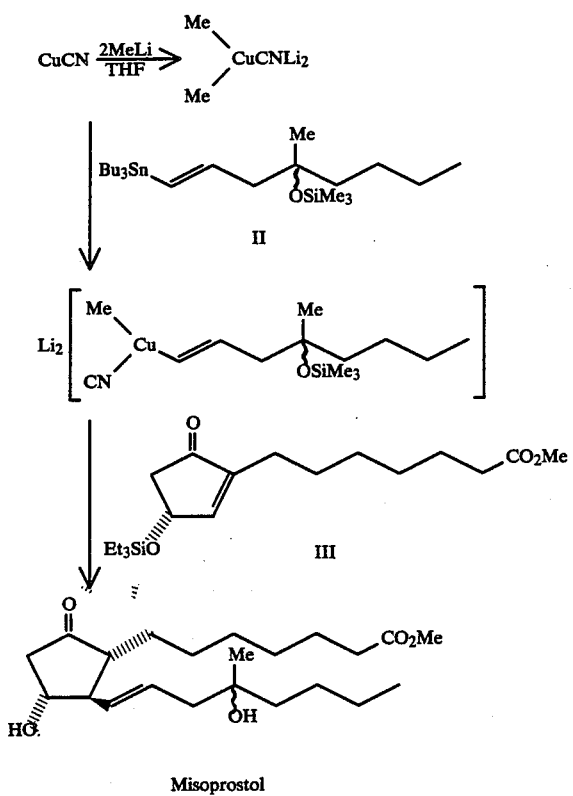

Misoprostol

In the examples below, the reaction and all transfers are done under an argon atmosphere and the tetrahydrofuran (THF) is non-stabilized. All glassware is flame dried under an argon atmosphere and all reagents are degassed with vacuum and purged with argon prior to their use. All quenches were performed in the presence of air.

EXAMPLE 1

In Situ Formation Of Methyl Vinyl Copper Cyanide To Prepare A Prostaglandin (Misoprostol)

To copper cyanide (1.75 g, 19.5 mmol, flame dried under vacuum after addition to a one necked 250 ml rounded bottom flask) is added tetrahydrofuran (26 ml). The resulting heterogeneous mixture is cooled to 0° C. and methyl lithium (27 ml. 1.5M in diethylether, 40.9 mmol) is added via syringe. During the addition, the temperature increases to 20°–22° C. and the mixture becomes homogeneous. To this mixture is added a solution of vinylstannane II, (11 g, 21.8 mmol) in tetrahydrofuran (26 ml) via cannula. The resulting homogeneous solution is stirred at ambient temperature until cuprate formation is complete as determined by vapor phase chromatography (VPC) analysis of a quenched aliquot, 1–3 hours normally. To this mixture, after cooling to −70° C., is added a solution of III, the triethylsilyl protected enone, (4.6 g, 13.0 mmol) in tetrahydrofuran (26 ml) via cannula (temperature increased to approx. −40° C.). The homogeneous reaction mixture is stirred cold for 5 minutes and then quenched by pouring into a saturated aqueous solution of ammonium chloride (150 ml) and concentrated ammonium hydroxide (15 ml). After stirring for approximately one hour, the aqueous layer (dark blue) is separated and the organic layer is washed with saturated NaCl (2×50 ml), dried ($Na_2SO_4$), and concentrated under vacuum to an oil. Following deprotection and chromatography, misoprostol is isolated in 90–95% yield.

EXAMPLE 2

In Situ Formation Of Butyl Vinyl Copper Cyanide To Prepare A Prostaglandin (Misoprostol)

Dibutyl copper cyanide is prepared according to the procedures of Example 1. To copper cyanide (1.75 g, 19.5 mmol, flame dried under vacuum after addition to a one necked 250 ml rounded bottom flask) is added tetrahydrofuran (26 ml). The resulting heterogeneous mixture is cooled to 0° C. and butyl lithium (16.4 ml, 2.5M in hexane, 40.9 mmol) is added via syringe. During the addition the temperature increases slowly and the mixture becomes homogeneous. To this mixture is added a solution of vinylstannane II, (11 g, 21.8 mmol), in tetrahydrofuran (26 ml) via cannula. The resulting homogeneous solution is stirred at ambient temperature until cuprate formation is complete (determined by VPC analysis of quenched aliquot, 1–3 hours normally). To this mixture, after cooling to −70° C., is added a solution of the triethylsilyl protected enone III, (4.6 g, 13.0 mmol) in tetrahydrofuran (26 ml), via cannula (temperature increases to approx. −40° C.). The homogeneous reaction mixture is stirred cold for 5 minutes and then quenched by pouring into a saturated aqueous solution of ammonium chloride (150 ml) and concentrated ammonium hydroxide (15 ml). After stirring for approximately one hour the aqueous layer (dark blue) is separated and the organic layer is washed with saturated NaCl (2×50 ml), dried ($Na_2SO_4$), and concentrated under vacuum to an oil. Following deprotection and chromatography, misoprostol is isolated.

EXAMPLE 3

In Situ Formation Of Methyl Vinyl Copper Thiocyanate To Prepare A Prostaglandin (Misoprostol)

Dimethyl copper thiocyanate is prepared in the following manner. To copper thiocyanate (687.1 mg, 5.65 mmol, flame dried under vacuum after addition to a one necked 250 ml rounded bottom flask) is added tetrahydrofuran (10 ml). The resulting heterogeneous mixture is cooled to 0° C. and methyl lithium (8.9 ml, 1.4M in diethylether, 12.4 mmol) is added via syringe. During the addition, the temperature increases slowly and the mixture becomes homogeneous. To this mixture is added a solution of vinylstannane II, (4.05 g, 8.05 mmol), in tetrahydrofuran (5 ml) via cannula. The resulting homogeneous solution is stirred at ambient temperature until cuprate formation is complete as determined by VPC analysis of a quenched aliquot, 1-3 hrs. normally. To this mixture, after cooling to −70° C., is added a solution of the triethylsilyl protected enone III, (1.3 g, 3.8 mmol) in tetrahydrofuran (5 ml) via cannula (temperature increases to approx. −40° C.). The homogeneous reaction mixture is stirred cold for 5 min. and then quenched by pouring into a saturated aqueous solution of ammonium chloride (20 ml) and concentrated ammonium hydroxide (2 ml). After stirring for approximately one hour, the aqueous layer (dark blue) is separated and the organic layer is washed with saturated NaCl (2×25 ml), dried ($Na_2SO_4$), and concentrated under vacuum to an oil. Following deprotection and chromatography, misoprostol is isolated.

EXAMPLE 4

In Situ Formation Of Vinyl Thienyl Copper Cyanide To Prepare A Prostaglandin (Misoprostol)

Methyl thienyl copper cyanide is prepared in the following manner. To copper cyanide (756 mg, 8.46 mmol) flame dried under vacuum is added THF (10 ml) and methyllithium (7.25 ml, 1.4M in diethylether, 10.1 mmol) followed by a THF (10 ml) solution of 2-lithio thiophene previously prepared by treating thiophene (712 mg, 846 mmol) in 10 ml of THF cooled to −60° C. with n-butyllithium (2.5M in hexane, 3.4 ml, 8.46 mmol). Optionally, the thienyl copper cyanide can be prepared and stored prior to use. To this mixture is added a solution of vinylstannane II, (6.08 g, 12 mmol) in THF (10 ml) via cannula. The resulting homogeneous solution is stirred for 1-3 hours at ambient (25° C.) temperature after which VPC analysis indicates complete cuprate formation. Addition of a THF solution of triethylsilyl protected enone III, to an aliquot of this solution at −70° C. indicates (TLC analysis) complete enone consumption and misoprostol formation.

EXAMPLE 5

In Situ Formation Of Methyl Allyl Copper Cyanide

Dimethyl copper cyanide is prepared in the following manner. To copper cyanide (100 mg, 1.12 mmol) flame dried under vacuum in a single necked round bottom flask, is added tetrahydrofuran (5 ml). The resulting heterogeneous mixture is cooled to 0° C. and methyllithium (1.38M in diethylether, 17 ml, 2.35 mmol) is added via syringe. To this mixture is added a solution of tetra-allyl tin (80 mg, 0.28 mmol) in tetrahydrofuran (4 ml). The resulting solution is allowed to stir for 1.5 hours at ambient (23° C.) temperature after which TLC analysis of a quenched aliquot indicated complete cuprate formation. To this mixture, after cooling to −70° C., is added a solution of 4-(tertbutyldimethylsilyloxy)-cyclopentenone (238 mg, 112 mmol) in tetrahydrofuran (1 ml). The resulting reaction mixture is stirred cold for 20 minutes and then quenched into a solution of saturated aqueous ammonium chloride (30 ml) and concentrated ammonium hydroxide (3.0 ml). After stirring for one hour, the layers are separated and the organic layer is washed with saturated aqueous sodium chloride solution (5.0 ml), dried over sodium sulfate and concentrated under vacuum to an oil. Following chromatography, the conjugate 1,4-addition product is isolated in 41% yield and the 1,2-addition products are isolated in 48% yield.

EXAMPLE 6

In Situ Formation Of Methyl, Fluorovinyl Copper Cyanide

To copper cyanide (18 mg, 0.2 mmol) in THF (0.75 ml) is added the fluorovinylstannane, IV. The heterogeneous mixture is cooled to 0° C. and methyllithium (1.251M in diethylether, 400 μL, 0.5 mmol) is added. The resulting homogeneous mixture is stirred at ambient temperature (20°-25° C.) for 1 hour. TLC analysis of a quenched aliquot indicated complete cuprate formation. The reaction is cooled to −78° C. and a solution of the triethylsilyl protected cyclopentenone III, in THF (0.75 ml) is added via cannula. After 30 minutes, the reaction is quenched in a solution of saturated ammonium chloride (9 ml) and concentrated ammonium hydroxide (1 ml). The aqueous mixture is extracted with diethylether (3×10 ml). The combined ether layers are washed with saturated aqueous sodium chloride (10 ml), dried over sodium sulfate and concentrated to an oil. Following deprotection and chromatography, 17-fluoro-misoprostol can be isolated in 50% yield.

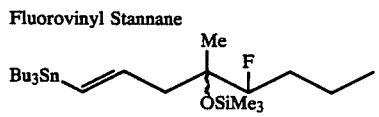

Fluorovinyl Stannane    IV

EXAMPLE 7

According to the process of Example 1, a 1:1 mixture of (11R, 16S) and (11S, 16R)-enisoprost is prepared from optically pure 4-methyl, 4-silyloxyvinyl stannane and racemic tiethylsilyl enone.

EXAMPLE 8

Preparation of Methylvinyl Copper Cyanide

To copper cyanide (1.01 g, 11.3 mmol) is added tetrahydrofuran (20 ml) and to this heterogeneous mixture, is cooled to 0° C., is added methyllithium (1.4M in diethylether, 17.8 ml, 25 mmol), the temperature rises to 20°-22° C. To this homogeneous mixture is added a tetrahydrofuran (THF, 10 ml) solution of vinylstannane II, (8.1 g, 13 mmol), via cannula. The resulting solution is stirred for 1-3 hours after which VPC analysis of a quenched sample indicated complete cuprate formation. The resulting cuprate solution, calculated to be 0.297M, is transferred via cannula to a dried, septum capped bottle under an inert atmosphere of argon and stored at −5° C. This solution is used from time to time according to the processes of Examples 9 and 10, or alternatively can be used immediately after preparation.

EXAMPLE 9

Preparation of 7-hydroxyenisoprost

To a standard solution (stored at 0° C. for 1-30 days) of methyl vinyl copper cyanide from Example 8 (6.3 ml, 0.3M in tetrahydrofuran/diethyl ether:2.7/1.0, 1.9 mmol) cooled to −65° C. is added, via cannula, a solution of 4-dimethyl-t-butylsilyloxy-cyclopentnenone. To this homogeneous mixture, after stirring for 15 minutes at −65° C., is added via cannula, a solution of (Z)-methyl-7-oxo-hept-4-eneoate in tetrahydrofuran (2 ml). Stirring is continued at −65° C. for 45 minutes followed by quenching into a solution of saturated ammonium chloride (15 ml) and ammonium hydroxide (1.5 ml). This aqueous mixture is extracted with diethylether (2×25 ml). The organics are combined, washed with saturated sodium chloride (2×25 ml), dried over sodium sulfate, and concentrated to an oil. After deprotection and chromatography 7-hydroxyenisoprost is isolated in 35–65% yield.

EXAMPLE 10

Synthesis of 7-hydroxy-misoprostol

According to the process of Example 9, 7-hydroxy-misoprostol can be prepared in 38–50% yield from 4-dimethyl-t-butylsilyloxy-cyclopentenone, vinyl methyl copper cyanide, and methyl-7-oxo-heptanoate.

The above examples illustrate the invention and are not intended to limit the invention or scope.

What is claimed is:

1. A process for preparing a higher order cuprate complex comprising bringing into reactive contact a first cuprate complex of the formula:

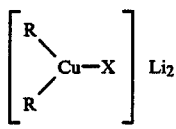

or

wherein:
(a) X is —CN, —SCN, —OSO$_2$CF$_3$, or —S—phenyl;
(b) each R is independently lower alkyl, alkenyl, phenyl, naphthyl, phenanthryl, or thienyl, provided that (i) each of the aforementioned radicals may be substituted with non-interfering substituents and (ii) only one R in the first cuprate complex may be alkenyl, phenyl, naphthyl, phenanthryl, or thienyl; and
(c) each R$^1$ is independently lower alkyl;
with a stannane compound of the formula:

wherein R$_t$ is a carbanion for carbon to carbon bond formation reactions and is not the same as any R in the first cuprate complex and each R$^2$ is independently lower alkyl or R$_t$;
whereby R$_t$ replaces at least one R on Cu.

2. A process for preparing a higher order cuprate complex according to claim 1, wherein a first cuprate complex of the formula

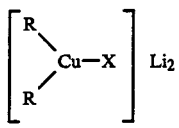

is brought into reactive contact with

in an ether, alkane, or mixture of ether/alkane solvent at about −20° C. to about 30° C., wherein R are each independently lower alkyl or one R is lower alkyl and the other is thienyl; X is —CN or —SCN; each R$^2$ is independently lower alkyl; and R$_t$ is a carbanion for carbon to carbon bond formation wherein R$_t$ displaces at least one R on the first cuprate complex.

3. A process according to claim 2 wherein R$_t$ is a vinyl carbanion.

4. A process according to claim 2 wherein R$_t$ is a benzyl or substituted benzyl carbanion.

5. A process according to claim 2 wherein R$_t$ is a allyl carbanion.

6. A process according to claim 2 wherein R$_t$ is a alkyl carbanion.

7. The process according to claim 2 wherein R$_t$ is the omega side chain of a natural or synthetic prostaglandin wherein the hydroxy groups are optionally protected with tri-lower-alkylsilyl, tetrahydropyranyl, or tetrahydrofuranyl.

8. A process according to claim 7 wherein R$_t$Sn(R$^2$)$_3$ is selected from the group consisting of:

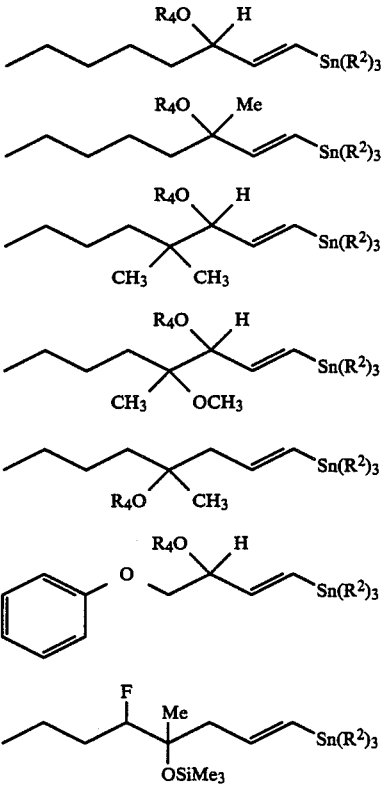

wherein R$_4$ represents tri-lower-alkylsilyl, tetrahydropyranyl, or tetrahydrofuranyl and each R$^2$ represents independently lower alkyl.

* * * * *

UNITED STATES PATENT AND TRADEMARK OFFICE
CERTIFICATE OF CORRECTION

PATENT NO. : 4,777,275
DATED     : October 11, 1988
INVENTOR(S) : Campbell, et al.

It is certified that error appears in the above-identified patent and that said Letters Patent is hereby corrected as shown below:

Column 3, the second structure, that portion of the structure reading

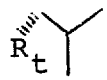  should read  

Signed and Sealed this

Third Day of April, 1990

*Attest:*

HARRY F. MANBECK, JR.

*Attesting Officer*   Commissioner of Patents and Trademarks